United States Patent [19]
Shearon et al.

[11] Patent Number: 5,919,188
[45] Date of Patent: Jul. 6, 1999

[54] LINEAR ABLATION CATHETER

[75] Inventors: Larry W. Shearon, Roseville, Minn.; Mark A. Maguire, San Jose, Calif.

[73] Assignee: Medtronic, Inc., Minneapolis, Minn.

[21] Appl. No.: 08/794,066

[22] Filed: Feb. 4, 1997

[51] Int. Cl.⁶ .............................. A61N 1/05; A61B 5/04
[52] U.S. Cl. .......................... 606/41; 600/374; 607/122
[58] Field of Search ................... 606/32, 34, 41; 607/119, 122, 123; 600/372, 373, 374, 377, 381

[56] References Cited

U.S. PATENT DOCUMENTS

| | | |
|---|---|---|
| 517,180 | 3/1894 | Wilson . |
| 623,022 | 4/1899 | Johnson ................................. 607/133 |
| 3,815,604 | 6/1974 | O'Malley et al. . |
| 3,910,279 | 10/1975 | Okada et al. . |
| 4,976,711 | 12/1990 | Parins et al. . |
| 5,080,660 | 1/1992 | Buelna . |
| 5,098,431 | 3/1992 | Rydell . |
| 5,122,138 | 6/1992 | Manwaring . |
| 5,360,427 | 11/1994 | Majlessi . |
| 5,431,696 | 7/1995 | Atlee, III ................................ 607/124 |
| 5,487,385 | 1/1996 | Avitall .................................... 607/122 |
| 5,507,743 | 4/1996 | Edwards et al. . |
| 5,578,007 | 11/1996 | Imran ....................................... 606/15 |
| 5,607,462 | 3/1997 | Imran ..................................... 607/122 |
| 5,672,174 | 9/1997 | Gough et al. ............................ 606/41 |
| 5,676,693 | 10/1997 | LaFontaine ............................ 607/116 |
| 5,687,723 | 11/1997 | Avitall ...................................... 606/41 |
| 5,755,714 | 5/1998 | Murphy-Chutorian ................. 607/122 |

*Primary Examiner*—Kenneth E. Peterson
*Assistant Examiner*—David M. Ruddy
*Attorney, Agent, or Firm*—Townsend and Townsend and Crew LLP

[57] ABSTRACT

A linear ablation catheter assembly (2) includes a handle (4) from which a hollow outer shaft (8) extends. A hollow inner catheter (10) is slidably housed within the outer shaft. The handle has a manipulator (18) which moves the inner catheter along the interior of the outer shaft. The inner catheter has an opening (22) alignable with and movable along a longitudinally-extending opening (14) formed in the hollow outer shaft. A typically perforated, electrode is mounted to the inner catheter (10, 17; 10a, 17a) or the outer shaft (10b, 17b) is spaced-apart from the outer surface (30) of the outer shaft. The handle is coupled to a source (28) of energy-conducting liquid (29) which flows through the inner catheter, out the inner catheter opening, past the perforated electrode, between fluid seals (32, 32c) secured to the inner shaft and through the longitudinally-extending opening to ablate tissue. Moving the inner catheter opening along the longitudinally-extending opening causes a longitudinally-extending lesion to be created.

23 Claims, 2 Drawing Sheets

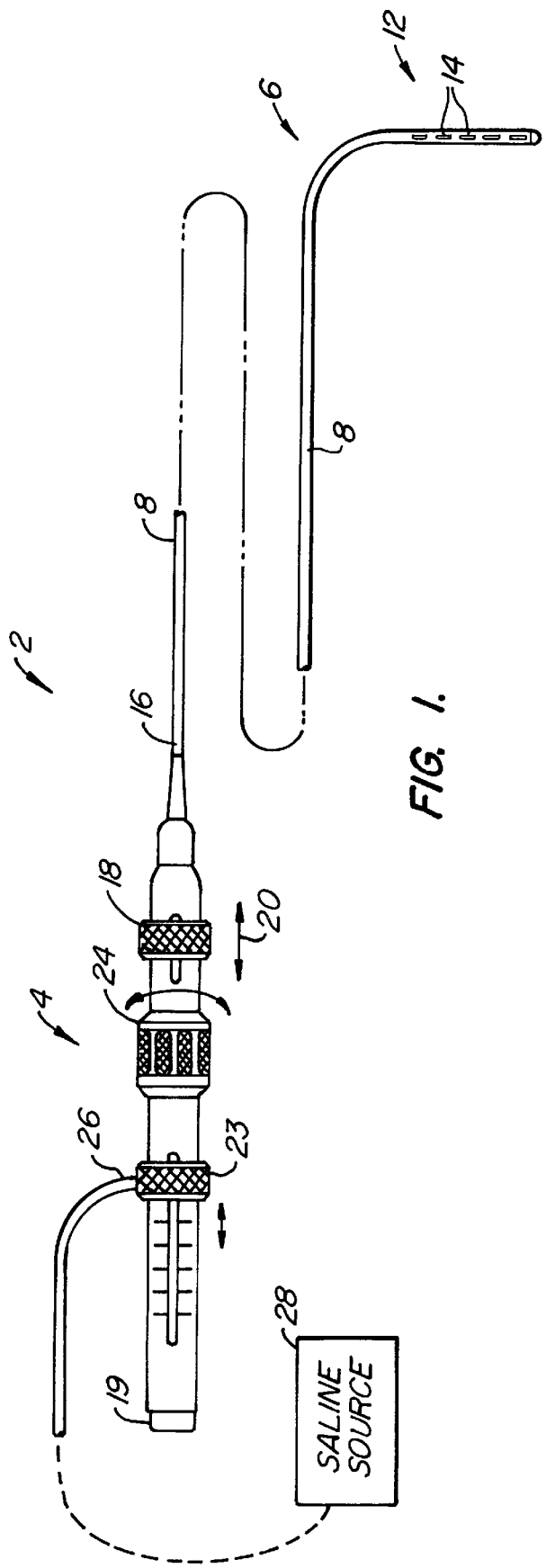
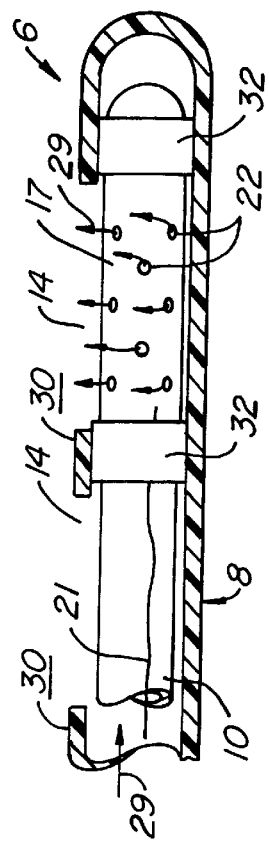
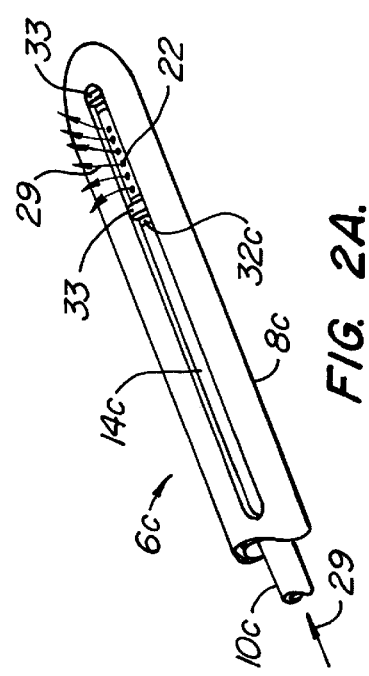
FIG. 1.
FIG. 2.
FIG. 2A.

LINEAR ABLATION CATHETER

CROSS-REFERENCE TO RELATED APPLICATIONS

This application is related to U.S. patent application Ser. No. 08/794,804, entitled "Systems and Methods for Tissue Mapping and Ablation, " (Attorney Docket 14875-002700), and U.S. patent application Ser. No. 08/794,803, entitled Fluid Cooled Ablation Catheter and Method for Making," (Attorney Docket 14875-003400), both filed on the same day as this application and both assigned to the same assignee, the disclosures of which are incorporated by reference.

BACKGROUND OF THE INVENTION

The invention relates to catheters, and more particularly to ablation catheters capable of creating linear lesions.

It has long been known that the action of the heart depends on electrical signals within the heart tissue. Sometimes these electrical signals become faulty. It has been found that ablating (burning) these cardiac conduction pathways in the region of the problem destroys the tissue to eliminate the faulty signal. Ablation is also used therapeutically with other organ tissue, such as the liver, prostate and uterus.

Electrophysiology (EP) catheters are catheters having one or more electrodes at their tips and are used for both diagnosis and therapy. Electrodes at the tips of EP catheters allow the physician to measure electrical signals along the surface of the heart (called mapping) then, when necessary, ablate certain tissues using, typically, radio frequency (RF) energy conducted to one or more ablation electrodes.

Sometimes ablation is necessary only at discrete positions along the chamber wall. This is the case when ablating accessory pathways, such as in Wolff-Parkinson-White syndrome or AV nodal reentrant tachycardias. At other times, however, ablation is desired along a line, called linear ablation. This is the case for atrial fibrillation, where the aim is to reduce the total mass of contiguous (electrically connected) atrial tissue below a threshold believed to be critical for sustaining multiple reentrant wavelets. Linear lesions are created between electrically non-conductive anatomic landmarks to reduce the contiguous atrial mass.

Linear ablation is typically accomplished in one of several ways. One way is to position the tip portion of the catheter so that an ablation electrode is located at one end of the target site, apply energy to the electrode to ablate the tissue adjacent to the electrode and then slide the tip portion along the chamber wall and repeat the ablation sequence. This is sometimes referred to as the burn-drag-burn technique. This technique is time-consuming (which is not good for the patient) and requires multiple accurate placements of the electrode (which may be difficult for the physician). Another way is to use a catheter having the series of spaced-apart band or coil electrodes which, after the electrode portion of the catheter has been properly positioned, are energized simultaneously or one at a time to create the desired lesion. If the electrodes are close enough together the lesions run together sufficiently to create a continuous linear lesion. While this technique eliminates some of the problems associated with the burn-drag-burn technique, some repositioning of the catheter may be required to create an adequately long lesion. In addition, it may be difficult to obtain adequate tissue contact pressure for each electrode in a multi-electrode catheter. Also, the use of multiple electrodes to create the linear lesion tends to make the tip portion more expensive to make, more bulky and may cause the tip portion to be stiffer than is possible when a single, or very few, electrodes are used. The added complications resulting from the use of multiple ablation electrodes can also reduce overall reliability.

Another ablation-related problem results from the delivery of RF energy to muscular tissue, such as the heart. Ablation of such tissue using conventional ablation catheters has a tendency to char or burn the contacting blood or tissue with which the electrodes are in contact if the temperatures exceed a certain threshold (generally 100° C.). This increases the difficulty of the ablation process by necessitating removal of the catheter to clean the tip portion after a series of burns.

SUMMARY OF THE INVENTION

The present invention is directed to a linear ablation catheter which uses an energy-conducting liquid to direct ablation energy to the tissue to be ablated. The resulting tip portion can be simpler in construction, more flexible, and less expensive than metal electrode linear ablation catheters.

A linear ablation catheter assembly includes a handle from which a hollow outer shaft tubing extends. A hollow inner catheter is preferably slidably housed within the outer shaft. The handle has an inner catheter longitudinal manipulator operably coupled to the inner catheter to permit the distal portion of the inner catheter to be moved along a longitudinally-extending opening formed in the outer shaft. The distal portion of the inner catheter has an opening alignable with and movable along the longitudinally-extending opening formed in the hollow outer shaft. Alternatively, the inner member could be fixed to the handle and the outer shaft slidably connected to a handle control. In either case the result is relative longitudinal movement between the inner catheter and the outer shaft.

The handle is coupleable to a source of energy-conducting liquid. The energy-conducting liquid is directable through the inner catheter, out the opening at the distal portion of the inner catheter and through the longitudinally-extending opening in the hollow outer shaft. An electrode (typically on RF emitting electrode) is located along the flow path of the energy-conducting liquid at the longitudinally-extending opening. The electrode is positioned so as to be close to but not in contact with the tissue to be ablated. This positioning causes the energy-conducting liquid to become charged so the liquid acts as the ablation electrode. Moving the distal portion of the inner catheter along the longitudinally-extending opening causes a longitudinally-extending lesion to be created opposite the longitudinally-extending opening in the outer shaft without the need to move the outer shaft.

A primary advantage of the present invention is that it is a simpler catheter than those which employ multiple electrodes to create a linear lesion. The invention also reduces the likelihood of the need to remove the catheter and clean the tip after a series of burns. This is possible because the ablation electrodes are shrouded in, for example, saline instead of blood which can coagulate if overheated. Sticking of the ablation electrode to the tissue is also avoided with the invention. The construction also permits the tip portion of the catheter to be made more simply at less expense while achieving the desired flexibility. A tip portion made according to the present invention can be made to be extremely conformable to an irregular surface to create a highly conformable ablation electrode. In fact, the tissue is not contacted by the metal electrode, but rather is charged with ablation energy (RF) through direct contact of the ionic fluid (saline). In addition to delivery of the energy needed to ablate the tissue, the energy-conducting liquid could also be used to supply the target site with fluid for a chilled simulated lesion, or with an anesthetic, or with a drug having a desired electrophysiologic effect, or with heparin or steroids to prevent thrombus formation. The catheter could also emit a radiopaque dye for imaging the heart chambers or vessels, or for staining the tissue along the ablation line.

The present invention describes the hollow outer shaft as having a longitudinally-extending opening. This longitudinally-extending opening can be a series or set of spaced-apart apertures, a continuous slot, a series of slots or a length of porous material. In any event, an opening in the inner catheter shaft directs a flow of the energy-conducting liquid through the longitudinally-extending opening to create the longitudinally-extending lesion.

Other features and advantages of the invention will appear from the following description in which the preferred embodiments have been set forth in detail in conjunction with the accompanying drawings.

BRIEF DESCRIPTION OF THE DRAWINGS

FIG. 1 is a simplified overall view of a catheter assembly made according to the invention;

FIG. 2 is a simplified enlarged longitudinal cross-sectional view of the distal end of the tip portion of the catheter of FIG. 1;

FIG. 2A is an overall view of the distal end of the tip portion of an alternative embodiment of the invention;

DESCRIPTION OF THE PREFERRED EMBODIMENTS

Figure 3:
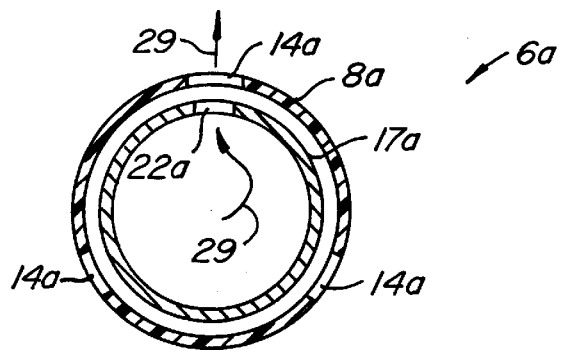
FIG. 3 is a transverse cross-sectional view of another embodiment of the invention illustrating the orientation of the three continuous slots in the outer sheath and showing the alignment of a longitudinally-extending opening in the inner catheter shaft with one of the three slots.

FIG. 1 illustrates a catheter assembly 2 designed to ablate tissue within the body. Typically the tissue will be endocardial or epicardial tissue, but other body organ tissue, such as the liver, can be ablated using the present invention. Catheter assembly 2 comprises a handle 4 from which a linear ablation catheter 6 extends. Linear ablation catheter 6 includes a hollow outer shaft 8 housing an inner catheter shaft 10 as shown in FIG. 2. Outer shaft 8 has a flexible tip portion 12 through which a number of longitudinally-extending slots or apertures 14 are formed. Outer shaft 8 also has a proximal end 16 mounted to and extending from handle 4. Inner catheter shaft 10 has a proximal end, not shown, coupled to a longitudinal manipulator 18 of handle 4. Movement of longitudinal manipulator 18 in the direction of arrow 20 causes inner catheter shaft 10 to move longitudinally within outer shaft 8.

Inner catheter shaft 10 has a perforated electrode (metal tip) 17 at its distal end. Electrode 17 is electrically coupled to an electrical connector 19 of handle 4 by a wire 21. Electrode 17 has a set of openings 22 which become aligned with the various apertures 14 formed in outer shaft 8 through the movement of longitudinal manipulator 18 for purposes to be discussed below.

Tip portion 12 of outer shaft 8 is preferably manipulatable by the user so that the tip portion can be deflected both axially and laterally. Axial deflection is accomplished by pushing or pulling on a manipulator wire (not shown) using an axial deflection manipulator 23 of handle 4. Lateral deflection, also known as torquing, of the tip portion is accomplished by rotation of a lateral manipulator 24; manipulator 24 is connected the tip portion 12 by a torque-transmitting core wire (not shown). See, for example, U.S. Pat. No. 5,487,757, the disclosure of which is incorporated by reference. Torquing could also be accomplished by rotating the entire handle 4. Thermocouple wires (not shown) are directed down inner catheter shaft 10 to permit temperature to be monitored.

Handle 4 also includes a liquid port 26 coupled to a saline source 28 at manipulator 23 to permit saline 29 to be supplied through port 26, along hollow inner catheter shaft 10, through openings 22 and then through apertures 14 as longitudinal manipulator 18 is moved in the direction of arrow 20. As is shown FIG. 2, electrode 17 is spaced-apart from the outer surface 30 of outer shaft 8. An ionic fluid, typically saline 29, passing through openings 22 becomes energized with, preferably, sufficient RF energy supplied by electrode 12 to ablate tissue (not shown) contacting surface 30. Seals 32 are positioned at both ends of electrode 17 to ensure that saline 19 passes through the aligned aperture 14 and not leak back down shaft 8. It is expected that electrode 17 needs to be positioned close to, preferably 0.013 mm to 2.0 mm from, and more preferably about 0.025 mm to 0.25 mm from, but not touching the tissues to be ablated. This permits tissue to be effectively ablated but eliminates the problems associated with ablation electrodes touching tissue, such as the need to clean fouled electrodes and electrodes sticking to ablated tissue. The presence of an ionic fluid layer between electrode 17 and the tissue to be ablated ensures that an ionic fluid layer conforming to the tissue contours is created. Openings 22 and apertures 14 are sized and configured so that the energized saline 29 creates a longitudinal lesion in the tissue adjacent to apertures 14. The use of slot-shaped apertures 14 helps to ensure a continuous lesion is created along the apertures. In some embodiments the longitudinal gap between apertures may be such that the lesions created at apertures 14 do not join up so that a true continuous lesion is not created with catheter 6 unless outer shaft 8 is moved after alignment of electrode 17 with each aperture 14. Therefore it is preferred that the gap between the apertures be short enough to ensure that a continuous lesion is created without the need to move outer shaft 8.

FIG. 2A illustrates an ablation catheter 6c having one long aperture 14c instead of the multiple apertures 14 of FIGS. 1 and 2. Seals 32c are similar to seals 32 but each seal 32c has a projection 33 which fits within aperture 14c to keep saline 29 from escaping along aperture 14c.

FIG. 3 illustrates an alternative embodiment of the invention in which apertures 14a have been formed in outer shaft 8a at three equally-space circumferential positions. Openings 22 have been replaced by a single longitudinally extending slot 22a formed in electrode 17a. With apertures 14a formed 120° apart from one another, outer shaft 8a can be more easily manipulated to ensure that one of the apertures 14a is aligned at the target site; the user would then rotate inner catheter shaft 10, and electrode 17a therewith, within outer shaft 8a so that opening 22 is aligned with the appropriate the aperture 14a.

Figure 4:
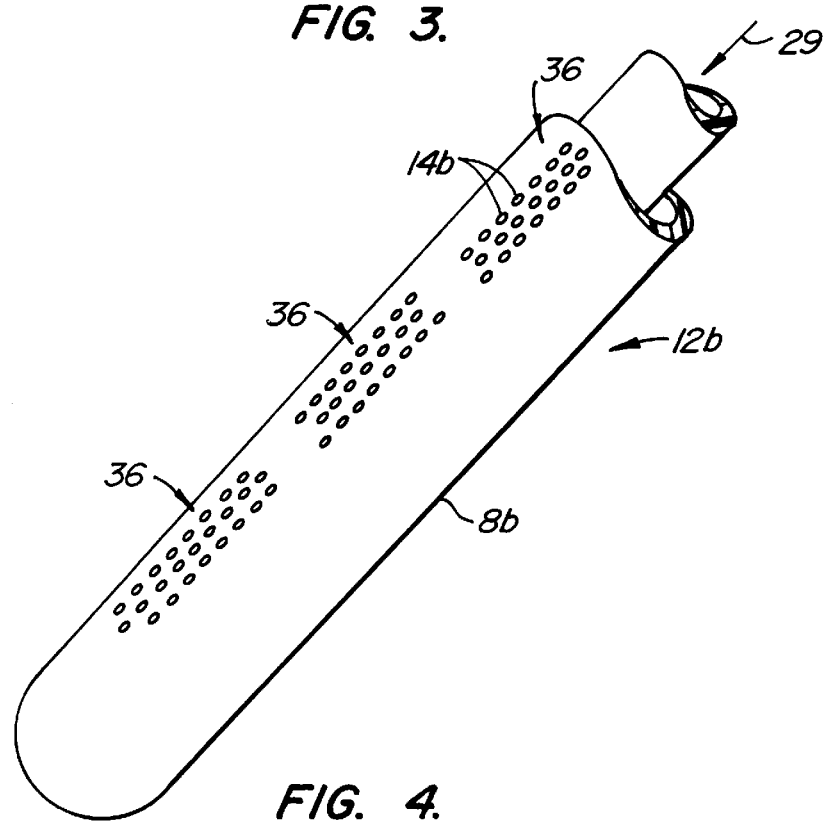
FIG. 4 is an overall view of the distal end of the tip portion of a further embodiment of the invention.
Figure 5:
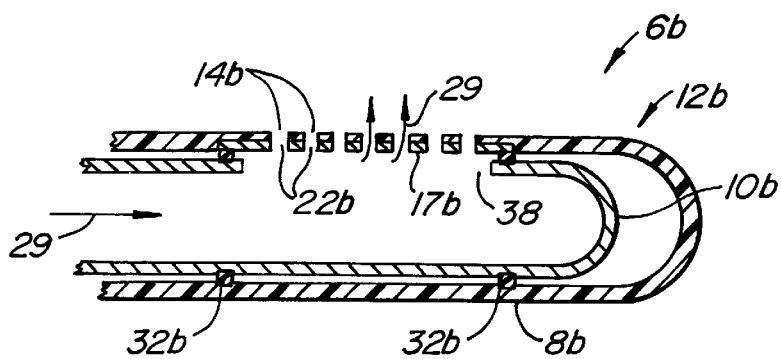
FIG. 5 is a longitudinal cross-sectional view of the embodiment of FIG. 4.

FIGS. 4 and 5 illustrate the tip portion 12b of an ablation catheter 6b similar to catheter 6 of FIGS. 1 and 2. Slotted apertures 14 of FIGS. 1 and 2 have been replaced by sets 36 of circular apertures 14b. Each set 36 of apertures 14b has an associated perforated, stationary electrode 17b mounted in the wall of outer shaft 8b, the perforations 22b of electrodes 12b being aligned with apertures 14b. Inner catheter shaft 10b has an axially-extending slotted opening 38 which can be aligned with sets 36 of apertures 14b. A flow of saline 29 is then passed through opening 38, through openings 22b in electrode 17b and through apertures 14b, whereupon the saline is energized by RF energy supplied to electrode 17b. In this embodiment electrode 17b is insulated from the tissue to be ablated by an outer portion of outer shaft 8b. O-ring seals 32b are used on each side of opening 22b to prevent excessive leakage of saline 29. It is preferred that each electrode 17b be energized independently of the other electrodes.

In use, tip portion 12 is directed to the target site so that the longitudinally-extending opening in the outer shaft, that is apertures 14, 14a or 14b, is properly positioned along the target site. Once in the proper position, saline 29 or other ionic fluid, can be directed through openings 22, 22a or 22b of electrodes 17, 17a or 17b, becoming a carrier for the RF current, and out through the longitudinally-extending opening to ablate the tissue aligned with such opening and create a linear lesion. Because there are no metal electrodes contacting the target tissue to char or burn the target tissue and because continuous fluid flow can keep the ablation catheter surface temperature below the threshold for blood coagulation, removal, cleaning and replacement of the ablation catheter may be eliminated or at least less necessary.

Modifications and variations can be made to the disclosed embodiments without departing from the subject of the invention as defined in the following claims. For example, saline 29 could be replaced by other energy-conducting liquid such as ringer's solution, ionic contrast, or even blood. Also, diagnostic or therapeutic agents, such as lidocaine CA ++ blockers or ionic contrast, could be delivered before, with or after the delivery of saline. Linear ablation catheter 6 could be made such that inner catheter shaft 10 is steerable instead of, or in addition to, outer shaft 8. In the preferred embodiments electrodes 17, 17a, 17b are all positionable adjacent to apertures 14, 14a and 14b during use. Depending upon, for example, the characteristics of the energy-conducting fluid, the size of apertures 14, 14a, 14b in the outer shaft and the fluid flow rate, the electrode could be much further away from the apertures; it may be possible to energize the fluid at source 28 or within inner catheter sheaft, or within handle 4 to eliminate the need for metal electrodes adjacent longitudinally-extending apertures 14, 14a, 14b. The opening(s) in outer shaft 8 could be defined by a porous material; the porous material could include a braided metal electrode. Also, inner shaft 10 could be made of a braided tube with the tip portion having an exposed metal braid electrode; the ionic fluid would then pass through the metal braid electrode for passage through the longitudinally extending opening in the outer shaft; such an embodiment may be easier to make and more flexible than a solid metallic inner shaft with holes in it. Seals 32, 32c could be made to be fixed to outer shaft 8, 8c instead of inner shaft 10, 10c.

What is claimed is:

1. A linear ablation catheter comprising:
   a hollow outer shaft having an outer surface and proximal and distal ends;
   at least one longitudinally-extending opening in the outer shaft towards the distal end of the outer shaft;
   a hollow inner shaft having a distal portion housed within the outer shaft;
   said outer and inner shafts being longitudinally slidable relative to one another;
   an electrode mounted to a chosen one of said outer shaft and inner shaft and positioned radially inwardly of the outer surfaces by a chosen distance; and
   said distal portion of said inner shaft comprising an opening alignable with and movable relative to the at least one longitudinally-extending opening through which an energy-conducting liquid can flow so a longitudinally-extending lesion can be created opposite the at least one longitudinally-extending opening.

2. The catheter according to claim 1 wherein the inner shaft is longitudinally slidable within the outer shaft.

3. The catheter according to claim 1 wherein at least one of the outer shaft and the inner shaft is steerable.

4. The catheter according to claim 1 wherein said at least one longitudinally-extending opening comprises a set of spaced-apart apertures.

5. The catheter according to claim 1 wherein said at least one longitudinally-extending opening comprises a continuous slot formed in the outer shaft.

6. The catheter according to claim 1 wherein said at least one longitudinally-extending opening comprises a plurality of longitudinally-extending openings positioned at different circumferential positions on said outer shaft.

7. The catheter according claim 1 further comprising a fluid seal positioned between the outer and inner shafts along the distal portion of the outer shaft.

8. The catheter according claim 1 wherein the chosen distance is between about 0.013 mm to 2.0 mm.

9. The catheter according to claim 8 wherein the chosen distance is between about 0.025 mm to 0.25 mm.

10. The catheter according claim 1 further comprising an electrode mounted to the outer shaft adjacent to the at least one longitudinally-extending opening.

11. The catheter according to claim 1 further comprising an electrode mounted to the inner shaft and positionable adjacent to the at least one longitudinally-extending opening.

12. The catheter according claim 11 wherein said electrode defines said opening in said inner shaft.

13. A linear ablation catheter assembly comprising:
   a handle coupleable to a source of energy-conducting liquid;
   a hollow outer shaft having an outer surface, a proximal end, extending from the handle, and a distal end;
   at least one longitudinally-extending opening in the outer shaft towards the distal end of the outer shaft;
   a hollow inner shaft having a distal portion slidably housed within the outer shaft;
   said handle comprising an inner shaft longitudinal manipulator operably coupled to the inner shaft so to permit the distal portion of the inner shaft to be moved along the at least one longitudinally-extending opening;
   said distal portion of said inner shaft comprising an opening alignable with and movable along the at least one longitudinally-extending opening;
   an electrode mounted to a chosen one of the outer shaft and inner shaft and positioned radially inwardly of from the outer surface; and
   an energy conductor extending between the electrode and the handle;
   whereby energy-conducting liquid can flow through said inner shaft, through said opening in said inner shaft, past the electrode and through said at least one longitudinally-extending opening to create a longitudinally-extending lesion opposite the at least one longitudinally-extending opening.

14. A linear ablation catheter assembly according to claim 13 wherein at least one of the outer shaft and the inner shaft is steerable.

15. A linear ablation catheter assembly according to claim 13 wherein said at least one longitudinally-extending opening comprises a plurality of longitudinally-extending openings positioned at different circumferential positions on said outer shaft.

16. A linear ablation catheter assembly according to claim 13 wherein said at least one longitudinally-extending opening comprises a continuous, longitudinally-extending slot.

17. A linear ablation catheter assembly according to claim 13 wherein the electrode is spaced apart from the outer surface by about 0.13 mm to 2.0 mm.

18. A linear ablation catheter assembly according to claim 13 further comprising a fluid seal positioned between the outer and inner shafts.

19. A linear ablation catheter comprising:
a hollow outer shaft having an outer surface and proximal and distal ends;
a longitudinally-extending opening in the outer shaft towards the distal end of the outer shaft;
a hollow inner shaft having a distal portion housed within the outer shaft;
said outer and inner shafts being longitudinally slidable relative to one another;
said distal portion of said inner shaft comprising an opening alignable with and movable relative to the longitudinally-extending opening;
an electrode mounted to a chosen one of said outer shaft and inner shaft and positioned radially inwardly of the outer surface; and
at least one fluid seal positioned between the outer and inner shafts and fixed to the inner shaft on either side of the opening in the inner shaft;
whereby an energy conducting liquid can flow through said openings so a longitudinally-extending lesion can be created opposite the longitudinally-extending opening.

20. A linear ablation catheter comprising:
a hollow outer shaft having an outer surface and proximal and distal ends;
a longitudinally-extending opening in the outer shaft towards the distal end of the outer shaft;
a hollow inner shaft having a distal portion housed within the outer shaft;
said outer and inner shafts being longitudinally slidable relative to one another;
said distal portion of said inner shaft comprising an opening alignable with and movable relative to the longitudinally-extending opening; an electrode mounted to a chosen one of said outer shaft and inner shaft and positioned radially inwardly of the outer surfacer; and
fluid seals positioned between the outer and inner shafts at spaced-apart positions along at least a portion of the longitudinally-extending opening to direct the flow of the energy-conducting liquid through the portion of the longitudinally-extending opening;
whereby an energy conducting liquid can flow so a longitudinally-extending lesion can be created opposite the longitudinally-extending opening.

21. A linear ablation catheter assembly comprising:
a handle coupleable to a source of energy-conducting liquid;
a hollow outer shaft having an armouter surface, a proximal end, extending from the handle, and a distal end;
a longitudinally-extending opening in the outer shaft towards the distal end of the outer shaft;
a hollow inner shaft having a distal portion slidably housed within the outer shaft, said distal portion of said inner shaft comprising an opening alignable with and movable along the longitudinally-extending opening;
said handle comprising:
an inner shaft longitudinal manipulator operably coupled to the inner shaft so to permit the distal portion of the inner shaft to be moved along the longitudinally-extending opening; and
a distal end deflection manipulator by which the distal end of the outer shaft can be radially deflected;
an electrode mounted to a chosen one of the outer shaft and inner shaft and positioned radially inwardly of the outer surface;
an energy conductor extending between the electrode and the handle; and
whereby energy-conducting liquid can flow through said inner shaft, through said opening in said inner shaft, past the electrode and through said longitudinally-extending opening to create a longitudinally-extending lesion opposite the longitudinally-extending opening.

22. A linear ablation catheter assembly comprising:
a handle coupleable to a source of energy-conducting liquid;
a hollow outer shaft having an outer surface, a proximal end, extending from the handle, and a distal end;
a longitudinally-extending opening in the outer shaft towards the distal end of the outer shaft;
a hollow inner shaft having a distal portion slidably housed within the outer shaft, said distal portion of said inner shaft comprising an opening alienable with and movable along the longitudinally-extending opening;
said handle comprising an inner shaft longitudinal manipulator operably coupled to the inner shaft so to permit the distal portion of the inner shaft to be moved along the longitudinally-extending opening;
an electrode mounted to a chosen one of the outer shaft and inner shaft and positioned radially inwardly of the outer surface;
an energy conductor extending between the electrode and the handle;
at least one fluid seal positioned between the outer and inner shafts and fixed to the inner shaft on either side of the opening in the inner shaft; and
whereby energy-conducting liquid can flow through said inner shaft, through said opening in said inner shaft, past the electrode and through said longitudinally-extending opening to create a longitudinally-extending lesion opposite the longitudinally-extending opening.

23. A linear ablation catheter assembly comprising:
a handle coupleable to a source of energy-conducting liquid;
a hollow outer shaft having an outer surface, a proximal end, extending from the handle, and a distal end;
a longitudinally-extending opening in the outer shaft towards the distal end of the outer shaft;
a hollow inner shaft having a distal portion slidably housed within the outer shaft, said distal portion of said inner shaft comprising an opening alignable with and movable along the longitudinally-extending opening;

said handle comprising an inner shaft longitudinal manipulator operably coupled to the inner shaft so to permit the distal portion of the inner shaft to be moved along the longitudinally-extending opening;

an electrode mounted to a chosen one of the outer shaft and inner shaft and positioned radially inwardly of the outer surface;

an energy conductor extending between the electrode and the handle;

fluid seals positioned between the outer and inner shafts at spaced-apart positions along at least a portion of the longitudinally-extending opening to direct the flow of the energy-conduction liquid through the portion of the longitudinally-extending opening; and whereby energy-conducting liquid can flow through said inner shaft, through said opening in said inner shaft, past the electrode and through said longitudinally-extending opening to create a longitudinally-extending lesion opposite the longitudinally-extending opening.

* * * * *